(12) United States Patent
Wang et al.

(10) Patent No.: US 7,967,962 B2
(45) Date of Patent: *Jun. 28, 2011

(54) SENSORS

(75) Inventors: Yi Wang, San Ramon, CA (US); Steve Scott, Pleasanton, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/463,211

(22) Filed: May 8, 2009

(65) Prior Publication Data

US 2009/0211923 A1    Aug. 27, 2009

Related U.S. Application Data

(63) Continuation of application No. 11/282,001, filed on Nov. 17, 2005, now Pat. No. 7,918,975.

(51) Int. Cl.
*G01N 27/327* (2006.01)
(52) U.S. Cl. .................. 204/403.01; 205/792
(58) Field of Classification Search .............. 204/400, 204/403.01–403.06, 403.09–403.14; 205/779, 205/792, 775
See application file for complete search history.

(56) References Cited

U.S. PATENT DOCUMENTS

| | | | |
|---|---|---|---|
| 6,071,391 A | 6/2000 | Gotoh et al. | |
| 6,120,676 A | 9/2000 | Heller et al. | |
| 6,143,164 A | 11/2000 | Heller et al. | |
| 6,287,451 B1 | 9/2001 | Winarta et al. | |
| 6,299,757 B1 | 10/2001 | Feldman et al. | |
| 6,338,790 B1 | 1/2002 | Feldman et al. | |
| 6,461,496 B1 | 10/2002 | Feldman et al. | |
| 6,503,381 B1 * | 1/2003 | Gotoh et al. | 204/403.14 |
| 6,551,494 B1 | 4/2003 | Heller et al. | |
| 6,576,101 B1 | 6/2003 | Heller et al. | |
| 6,591,125 B1 | 7/2003 | Buse et al. | |
| 6,592,745 B1 | 7/2003 | Feldman et al. | |
| 6,616,819 B1 | 9/2003 | Liamos et al. | |
| 6,618,934 B1 | 9/2003 | Feldman et al. | |
| 6,749,740 B2 | 6/2004 | Liamos et al. | |
| 6,923,894 B2 | 8/2005 | Huang et al. | |
| 6,942,518 B2 | 9/2005 | Liamos et al. | |
| 2002/0053523 A1 | 5/2002 | Liamos et al. | |
| 2002/0100685 A1 | 8/2002 | Huang et al. | |
| 2003/0196894 A1 | 10/2003 | Cai et al. | |

FOREIGN PATENT DOCUMENTS

| | | |
|---|---|---|
| EP | 0821784 | 11/1998 |
| EP | 0958495 | 11/2002 |
| EP | 1 548 427 A1 | 6/2005 |
| WO | 00/73778 | 12/2000 |
| WO | WO 03/091717 A1 | 11/2003 |
| WO | WO 2007/033007 A1 | 3/2007 |

OTHER PUBLICATIONS

1 Page from www.hemcue.com Website Illustrating Methods of Using a Sensor, available before Nov. 17, 2005. 3 Pages from www.hemcue.com Website Illustrating Methods of Using a Sensor, available before Nov. 17, 2005.
10 Pages from www.hemcue.com Website Illustrating Methods of Using a Sensor, available before Nov. 17, 2005.

* cited by examiner

*Primary Examiner* — Ula C Ruddock
*Assistant Examiner* — Gurpreet Kaur
(74) *Attorney, Agent, or Firm* — Edward J. Baba; Marcus T. Hunt; Bozicevic, Field & Francis LLP

(57) ABSTRACT

The subject invention provides devices and methods for the analysis of a body fluid. Embodiments include sensors that are sample-fillable by contacting a corner of the sensor to a sample.

34 Claims, 5 Drawing Sheets

SENSORS

CROSS-REFERENCE TO RELATED APPLICATIONS

This application is a continuation of U.S. patent application Ser. No. 11/282,001, filed on Nov. 17, 2005, which is incorporated herein by reference.

BACKGROUND OF THE INVENTION

Analytical sensors, e.g., test strips, are commonly used to determine the presence and concentration of an analyte in biological fluid. Such sensors may be used, for example, to monitor blood glucose levels of diabetic patients.

In using analyte sensors, an opening is created in the skin (e.g., by lancing the skin) to cause a flow of biological fluid from the region. At least a portion of this biological fluid is contacted to a sensor where the concentration of analyte in the fluid is then determined. Specifically, an opening in the skin is produced and an opening (i.e., a sample port) of the sensor is contacted to the expressed biological fluid to bring the fluid into contact with the sample chamber of the sensor where analysis occurs. The sample chamber is in fluid communication with the sample port.

Locating the sample port and contacting it with biological fluid is not without difficulty and becomes an even greater concern as the size of sample chambers are decreased to, e.g., decrease sample volumes, decrease test time, etc. Sample ports of conventional sensors are located on the top ("top fill"), the centered front end ("front-fill"), or a side ("side fill") of the sensors, which makes it difficult for a user to locate and contact with biological fluid. Users of such devices may have visual and/or dexterity problems, e.g., resulting from an underlying disease state such as diabetes, further compounding the difficulty in locating the sample port and positioning near a site of biological fluid.

The inability to easily locate the sample port and properly contact the sample to be tested with the sample port may not simply be a minor nuisance, but may have serious consequences. For example, in attempts to locate the sample port, the sample maybe smeared over the sensor surfaces resulting a difficult to handle sensor.

Sample smearing, and other factors associated with the inability to easily locate the sample port may have other serious consequences as well. For example, such may deplete the volume of sample available for testing so there may not be a sufficient amount of sample. A test may not begin and/or erroneous testing results may occur if an insufficient sample volume is present in the sample chamber. Insufficient sample volumes in the sample chamber may require the user to either "milk" the originally lanced site in an attempt to obtain more sample from the site or to lance an additional site. The user may associate both options with significant pain and may therefore elect instead to forego the testing. Foregoing testing may have serious health implications, e.g., it is desirable for a diabetic to test glucose levels multiple times throughout the day to sufficiently manage the diabetes.

Attempts have been made to address the above-described issues. For example, a test strip having cone-shaped channel entrance in the center of the front end of the test strip has been developed, but has not adequately addressed the problems and adds complexity to the manufacturing process.

Accordingly, as analyte sensors continue to be of importance in health management, there continues to be an interest in devices and methods that make testing easier, including testing devices and methods that enable a user to easily contact an analyte-containing sample with the sample chamber of the sensor. Of particular interest are analyte sensors and analyte testing methods that are easy and cost effective to manufacture and are easy to use, particularly for visually and/or dextrally impaired users.

SUMMARY OF THE INVENTION

The subject invention provides devices and methods for analyte testing such as analyte concentration determination in a biological fluid sample. Embodiments of the subject invention include corner-fill analyte sensors, e.g., corner-fill glucose sensors. Also provided are sensors adapted to minimize the distance between a sample chamber of the sensor and a peripheral edge of the sensor—a sample admitting edge of the sensor.

Embodiments of the subject devices include analyte sensors that include two or more intersecting edges and a sample chamber entrance positioned about an edge intersection. In certain embodiments, a sensor may include first and second opposing side edges and third and fourth opposing side edges (e.g., in the form of a rectangle), and a sample admitting port positioned about an intersection of any two edges of the sensor.

Aspects of the sensors of the subject invention include optical and electrochemical sensors. In many embodiments, the sensors are small-volume sensors. Small-volume sensors include sensors adapted to determine analyte concentration in a sample having a volume of about 1 microliter or less.

Also provided are methods for determining analyte concentration in a sample of biological fluid, where embodiments of the subject methods include applying an analyte-containing sample to a corner-fill analyte sensor by contacting a sample admitting opening positioned about a corner of the sensor with the sample, and determining the concentration of an analyte in the sample.

Embodiments of the subject methods also include contacting an edge intersection of an analyte sensor with sample, and determining the concentration of an analyte in the sample.

Also provided are systems and kits.

BRIEF DESCRIPTION OF THE DRAWINGS

FIGS. 2A, 2B and 2C show schematic exemplary embodiments of analyte sensors according to the subject invention wherein FIG. 2A shows a sensor having a sample chamber substantially parallel to the leading edge of the sensor, FIG. 2B shows a sensor having a sample chamber substantially perpendicular to the leading edge of the sensor, and FIG. 2C shows another sensor having a sample chamber substantially parallel to the leading edge of the sensor.

To facilitate understanding, identical reference numerals have been used, where practical, to designate the same elements which are common to different figures. The figures shown herein are not necessarily drawn to scale, with some components and features being exaggerated for clarity.

DEFINITIONS

Figures 1A, 1B:
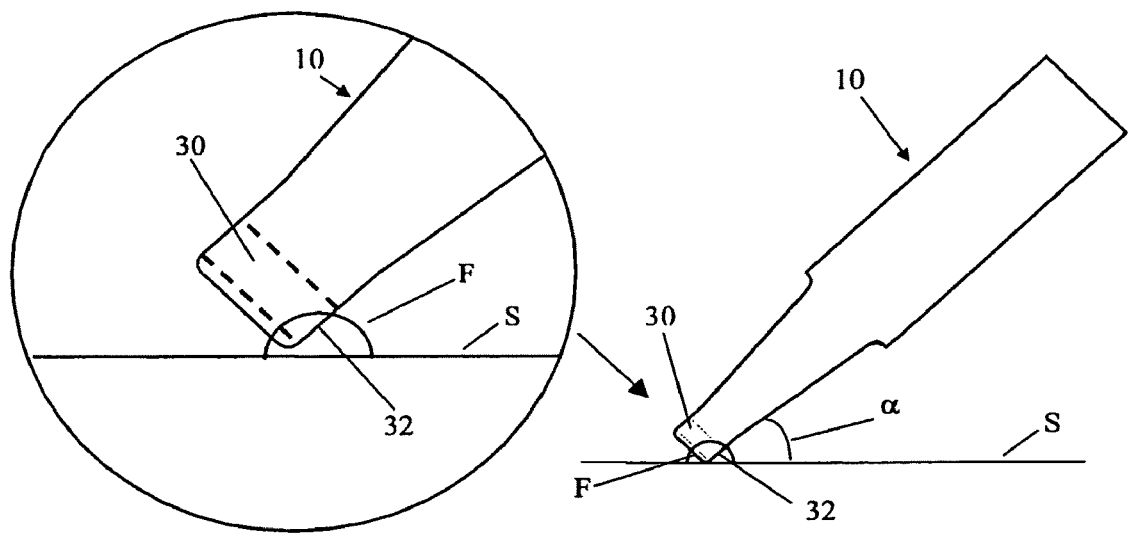
FIG. 1A shows a schematic exemplary embodiment of an analyte sensor according to the subject invention.
FIG. 1B shows an enlarged view of a portion of the sensor of FIG. 1A.

Throughout the present application, unless a contrary intention appears, the following terms refer to the indicated characteristics.

When two items are "associated" with one another they are provided in such a way that it is apparent that one is related to the other, such as where one references the other.

A "biological fluid", "physiological fluid" or "body fluid", or variations thereof, is any body fluid in which an analyte can be measured, for example, blood, interstitial fluid, dermal fluid, sweat, tears, and urine. "Blood" includes whole blood and its cell-free components, such as, plasma and serum.

"Communicating", "transmitting" and the like, of information reference conveying data representing information as electrical or optical signals over a suitable communication channel (for example, a private or public network, wired, optical fiber, wireless radio or satellite, or otherwise). Any communication or transmission can be between devices which are local or remote from one another.

A "computer", "processor" or "processing unit" are used interchangeably and each references any hardware or hardware/software combination which can control components as required to execute recited steps. For example, a computer, processor, or processor unit includes a general purpose digital microprocessor suitably programmed to perform all of the steps required of it, or any hardware or hardware/software combination which will perform those or equivalent steps. Programming may be accomplished, for example, from a computer readable medium carrying necessary program code (such as a portable storage medium) or by communication from a remote location (such as through a communication channel).

A "counter electrode" refers to an electrode, used in conjunction with a working electrode, through which passes an electrochemical current equal in magnitude and opposite in sign to the current passed through the working electrode. The term "counter electrode" is meant to include counter electrodes which also function as reference electrodes (i.e. a counter/reference electrode) unless the description provides that a "counter electrode" excludes a reference or counter/reference electrode.

An "electrochemical sensor" or "electrochemical sensor strip", and variations thereof, is a device configured to detect the presence of and/or measure the concentration of an analyte via electrochemical oxidation and reduction reactions. These reactions are transduced to an electrical signal that can be correlated to an amount or concentration of analyte.

"Electrolysis" is the electrooxidation or electroreduction of a compound either directly at an electrode or via one or more electron transfer agents (e.g., redox mediators and/or enzymes).

An "electron transfer agent" is a molecule that carries electrons between either a redox mediator and the analyte or the working electrode and the analyte. An electron transfer agent may be used in combination with a redox mediator.

The term "facing electrodes" or "opposing electrodes" refers to a configuration of the working and counter electrodes in which the working surface of the working electrode is disposed in approximate opposition to a surface of the counter electrode.

"Forwarding" an item refers to any means of getting that item from one location to the next, whether by physically transporting that item or using other known methods (where that is possible) and includes, at least in the case of data, physically transporting a medium carrying the data or communicating the data over a communication channel (including electrical, optical, or wireless).

An "indicator electrode" includes one or more electrodes that detect partial or complete filling of a sample chamber and/or measurement zone.

A "layer" includes one or more layers.

Items of data are "linked" to one another in a memory when a same data input (for example, filename or directory name or search term) retrieves those items (in a same file or not) or an input of one or more of the linked items retrieves one or more of the others.

"May" refers to optionally.

The "measurement zone" is defined herein as a region of the sample chamber sized to contain only that portion of the sample that is to be interrogated during an analyte assay.

A "memory" or "memory unit" refers to any device which can store information for retrieval as signals by a processor, and may include magnetic or optical devices (such as a hard disk, floppy disk, CD, or DVD), or solid state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices).

A "non-diffusible," "non-leachable," or "non-releasable" compound is a compound which does not substantially diffuse away from the working surface of the working electrode for the duration of the analyte assay.

A "diffusible," "leachable," or releasable" compound is a compound which substantially diffuses away from the working surface of the working electrode for the duration of the analyte assay.

The term "planar electrodes" or "co-planar electrodes" refers to a configuration of the working and counter electrodes in which the working surface of the working electrode is disposed at least approximately planar to a surface of the counter electrode. "Planar electrodes" or "co-planar electrodes" are typically located on the same substrate.

"Reading" signal data from a sensor refers to the detection of the signal data (such as by a detector or meter) from the sensor. This data may be saved in a memory (whether for relatively short or longer terms).

"Receiving" something means it is obtained by any possible means, such as delivery of a physical item. When information is received it may be obtained as data as a result of a transmission (such as by electrical or optical signals over any communication channel of a type mentioned herein), or it may be obtained as electrical or optical signals from reading some other medium (such as a magnetic, optical, or solid state storage device) carrying the information. However, when information is received from a communication it is received as a result of a transmission of that information from elsewhere (local or remote).

A "redox mediator" is an agent for carrying electrons between the analyte and the working electrode, either directly, or via an electron transfer agent.

A "reference electrode" includes a reference electrode that also functions as a counter electrode (i.e., a counter/reference electrode) unless the description provides that a "reference electrode" excludes a counter/reference electrode.

When an item is indicated as being "remote" from another, this is referenced that the two items are at least in different buildings, and may be at least one mile, ten miles, or at least one hundred miles apart. When different items are indicated as being "local" to each other they are not remote from one another (for example, they can be in the same building or the same room of a building).

A "working electrode" is an electrode at which analyte is electrooxidized or electroreduced with or without the agency of a redox mediator.

A "working surface" is the portion of a working electrode that is covered with non-leachable redox mediator and exposed to the sample, or, if the redox mediator is diffusible, a "working surface" is the portion of the working electrode that is exposed to the sample.

It will also be appreciated that throughout the present application, that words such as "cover", "base" "front", "back", "top", "upper", and "lower" are used in a relative sense only.

When two or more items (for example, elements or processes) are referenced by an alternative "or", this indicates that either could be present separately or any combination of them could be present together except where the presence of one necessarily excludes the other or others.

Any recited method can be carried out in the order of events recited or in any other order which is logically possible. Reference to a singular item, includes the possibility that there are plural of the same item present.

DETAILED DESCRIPTION OF EMBODIMENTS OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

Devices

As summarized above, embodiments of the subject invention includes corner-fill analyte sensors. By this it is meant sensors that are adapted to enable a user to fill the sample chamber (testing area) of the sensor with sample by contacting a corner of the sensor to a volume of sample. As mentioned above, sample filling a sensor at a sensor's corner is not possible with conventional sensors that are configured for end filling, top filling or side filling.

The sensors of the subject invention may be adapted to determine a wide variety of analytes, where glucose is primarily used herein for exemplary purposes only and is in no way intended to limit the scope of the invention. Additional analytes include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

The sensors are described primarily as electrochemical sensors for exemplary purposes only, where such description is in no way intended to limit the scope of the invention. It is to be understood that the sensors may be other than electrical sensor, e.g., optical sensors.

Figure 2A:
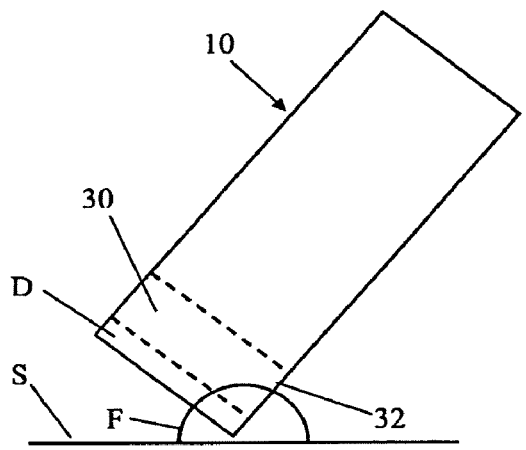
Figure 2B:
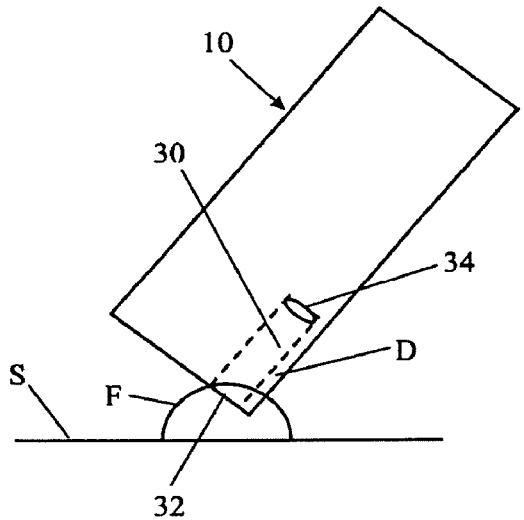
Figure 2C:
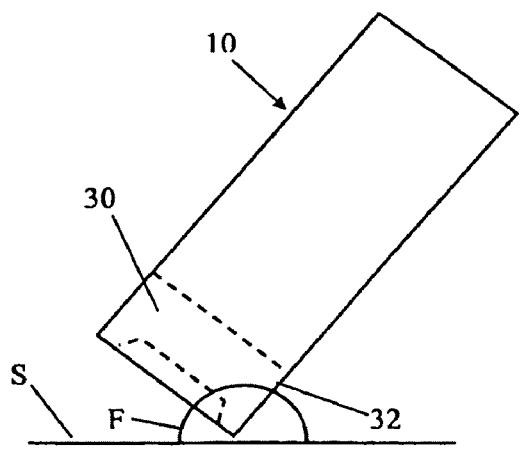

As shown in FIGS. 1A and 1B, which FIG. 1B is an enlarged view of a portion of FIG. 1A, a corner of a sensor 10 is contacted with a fluid sample F present on a surface S, such as a skin surface (see also FIGS. 2A, 2B and 2C, for example). An entrance 32 to the sample chamber 30 is located at or substantially near a corner of the sensor so that touching the corner to the fluid sample draws sample into sample chamber 30 via entrance 32. As described in greater detail below, at least a portion of one or more analyte-determining electrodes are present in the sample chamber. In this embodiment, the angle $\alpha$ formed by sensor 10 and surface S ranges from about 0° to about 90°, e.g., from about 30° to about 60°.

Accordingly to embodiments of the subject invention, an entrance, i.e., a port, to the sample chamber is positioned about a corner of the sensor. This positioning makes it easy for a user, who may have one or more physical impairments, to locate the entrance to the sample chamber by simply locating a corner of the sensor. Accordingly, the sample chamber may be easily filled with the appropriate amount of sample by simply touching a corner of the sensor to sample. The sample is thus drawn into the sample chamber, e.g., by capillary forces. The corners of a sensor may be rounded or square (e.g., forming substantially right angles or any other angles) and may include indents.

In certain embodiments, a sample chamber entrance may be at corner of the sensor and in other embodiments the sample chamber entrance may be substantially near, e.g., slightly displaced from or adjacent to, a corner of the sensor, e.g., a leading edge of the strip (also referred to as sample application edge). The distance from the leading edge of the sensor is minimized in the subject sensors, thereby enabling sample filling via one or more corners at the leading edge of the sensor. Minimizing the distance between the sample chamber and the distal edge not only provides an easy way for a user to located the sample chamber entrance, but also shortens sample filling time and thus overall assay time. For example, in order to perform an accurate test using the sensor, a minimum sample drop (i.e., minimum amount of sample) is necessary. Accordingly, in embodiments in which a sample chamber entrance is adjacent a corner, i.e., a corner-filling distance from the leading edge of the sensor, the distance between the leading edge of the sensor and a sample chamber entrance is extremely small, e.g., smaller than the radius of a sample drop to be contacted with the sensor. In certain embodiments, the distance (see for example distance D of FIGS. 2, 7 and 8) may range from about 0 mm to about 2.0 mm, e.g., 0.01 mm to about 1.0 mm, where in certain embodiments the distance may be about 0.3 mm. The distance from the meter connecting end of the sensor (the edge opposite the leading edge) to the sample chamber may range from about 10 mm to about 50 mm, e.g., from about 30 mm to about 40 mm.

In certain embodiments, more than one corner of a sensor includes a sample chamber entrance, e.g., two or more corners. A sensor may be in the form of a strip-commonly referred to as a test strip or sensor strip, e.g., analogous to FREESTYLE strips from Abbott Diabetes Care Inc., having a quadrilateral four sided form (e.g., square or rectangular). A test strip of the subject invention may be described as having a rectangular form with a first part or first end for sample filling and a second, e.g., opposite, part or second end for electrical coupling to a meter to be used with the strip. The sample filling end of a rectangularly-shaped, or the like, sensor includes two corners at the leading or sample application edge (i.e., an edge that is substantially transverse to the longitudinal axis). An entrance to the sample chamber may be positioned about one of the corners of the leading edge or may be positioned about both of the corners. For example, one or both corners may include a sample chamber entrance, or a sample chamber entrance may be slightly displaced from one or both of the corners (slightly set back from the leading edge of the sensor). In many embodiments, a sensor, e.g., a test strip, includes two sample chamber entrances and a first entrance is positioned about a first corners and a second entrance is positioned about a second corner, the second corner being on the substantially opposite side of the sensor from the first corner. A sample chamber may traverse the entire width of a sensor from a first side to an opposite second side, e.g., may be substantially transverse to the longitudinal axis of the sensor and traverse the entire width of the sensor, as shown in FIGS. 1A, 1B and 2A and 2C for example. The sample chamber may terminate at each, or just one, side of the sensor in an opening.

In certain embodiments, a sample chamber may be substantially parallel to the longitudinal axis of the sensor. FIGS. 2A, 2B and 2C show three exemplary embodiments of analyte sensors according to the subject invention. FIGS. 2A and 2C show a sensor having a sample chamber 30 substantially transverse to the longitudinal axis of the sensor. In the embodiments of FIGS. 2A and 2C, sample chamber 30 extends to both side edges for venting. FIG. 2B shows a sensor having a sample chamber 30 substantially parallel to the longitudinal axis of the sensor and in this embodiment including a vent 34. As shown, sample F may be admitted to the sample chamber of each sensor by contacting the corner of the sensor to the sample. As noted above, the distance D of each sensor may be less than the radius of the fluid sample drop F.

The sample chamber entrance may be positioned about any two or more edge intersections or junctions of a sensor. Specifically, a sensor may be characterized by its edges or sides. The edges may be linear or non-linear, and a certain of which may intersect. A sample chamber entrance may be located about an edge intersection so that contacting the edge intersection to a volume of sample draws sample into the sample chamber for testing.

The analyte sensors of the present invention may be adapted to measure the concentration of an analyte in any volume of sample, but are particularly useful in the determination of analyte concentration in a small volume of sample, e.g., a sample having a volume no more than about 1 µL, for example no more than about 0.5 µL, for example no more than about 0.25 µL, for example no more than about 0.1 µL. In some embodiments, the volume of sample may be as low as 0.05 µL or as low as 0.03 µL. The sensors of the subject invention may be configured as those described in U.S. patent application Ser. No. 11/225,659, the disclosure of which is herein incorporated by reference, in which an accurate analyte measurement may be obtained using a volume of sample that wholly or partially fills the sample chamber.

Figure 3:
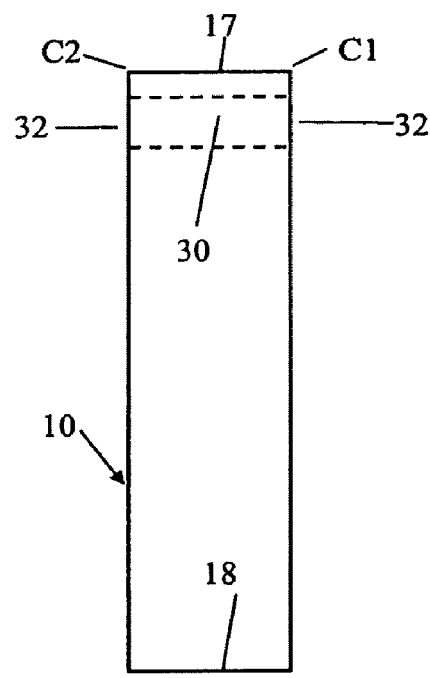
FIG. 3 shows a top view of a schematic exemplary embodiment of an analyte sensor according to the subject invention having a substantially constant width.
Figure 4:
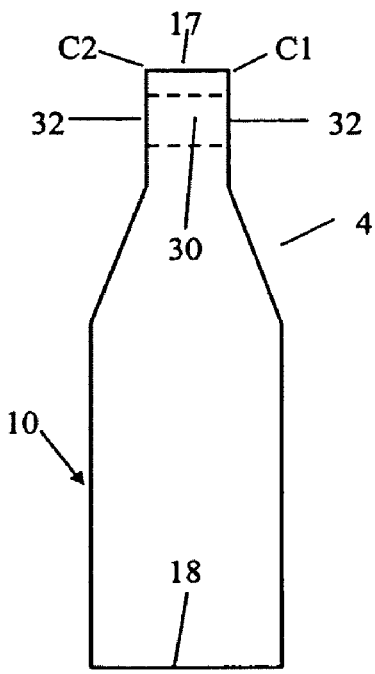
FIG. 4 shows a top view of a schematic exemplary embodiment of an analyte sensor according to the subject invention having a variable width.
Figure 5:
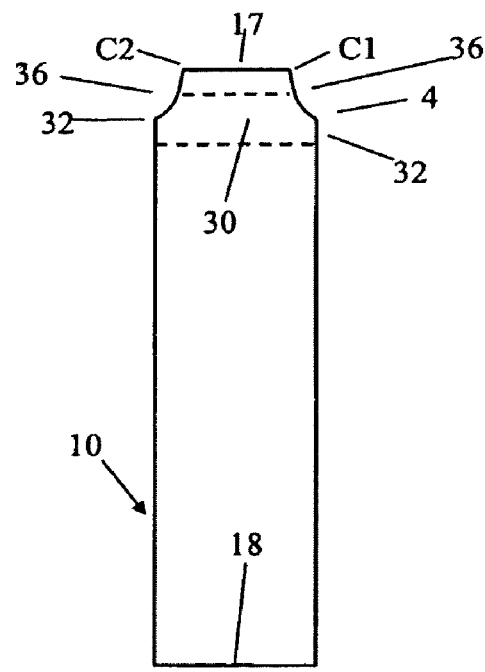
FIG. 5 shows a top view of another schematic exemplary embodiment of an analyte sensor according to the subject invention having a variable width and having indents.
Figure 6:
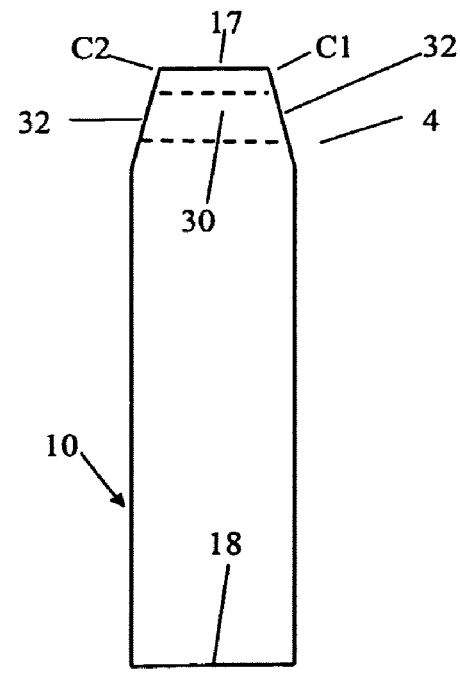
FIG. 6 shows a top view of another schematic exemplary embodiment of an analyte sensor according to the subject invention having a variable width.
Figure 7:
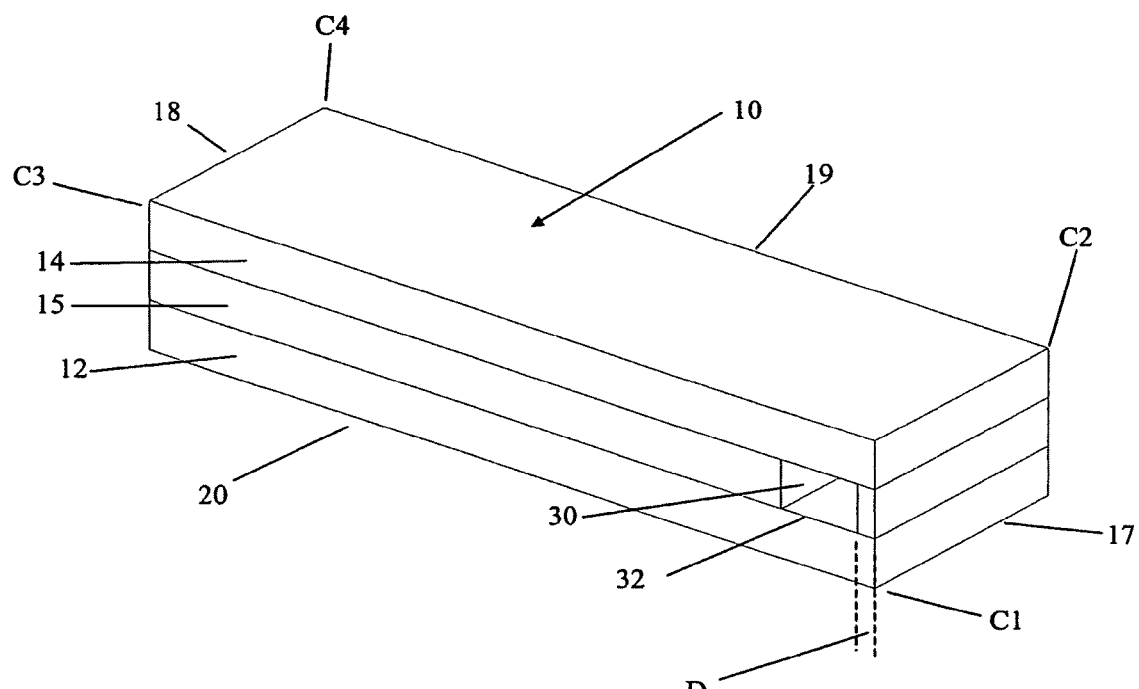
FIG. 7 shows a perspective view of the analyte sensor of FIG. 3.

Referring now to the Figures, FIGS. 3, 4, 5 and 6 schematically show plan views of exemplary embodiments of a sensor 10 of the invention and FIG. 7 shows a perspective view of sensor 10 of FIG. 3. The sensors of FIGS. 3, 4, 5 and 6 are substantially similar except that the sensor of FIG. 4 includes a shoulder 4, the sensor of FIG. 5 includes a shoulder 4 in the form of two finger-nesting indents 36, and the sensor of FIG. 6 includes gradually reduced tapered shoulders 4. The sample chambers 30 of sensors of FIGS. 3 and 4 and 6 terminate substantially close to the corners C1 and C2 and the leading edge 17 of the sensor and the sample chamber 30 of sensor 10 of FIG. 5 terminates at the corners C1 and C2 (see also the sensor of FIG. 2C which has a sample chamber that terminated at the corners C1 and C2).

As best shown in FIG. 7, sensor 10 includes a first substrate 12, a second substrate 14, a spacer 15 positioned therebetween, and a sample chamber 30 having an entrance 32. As will be described below, sensor 10 includes at least one working electrode and at least one counter electrode. Sensor 10 is a layered construction, in this particular embodiment having a generally rectangular shape, i.e., its length is longer than its width, although other shapes are possible as well, e.g., square, triangle, irregular shapes, complex shapes, etc.

Sensor 10 may be characterized by its edges or sides, 17, 18, 19 and 20 (for a quadrilateral sensor). A first edge 19 and a second opposite edge 20 are substantially parallel to an axis of the sensor. A third edge 17, herein referred to an the distal edge, leading edge or sample application or filling edge or end, and an opposite fourth edge 18, herein referred to as the proximal edge or meter connecting edge or end, are substantially transverse to an axis of the sensor. As shown, the intersections of edges 19 and 20 and the distal edge provide two distal corners and the intersection of edges 19 and 20 and the proximal edge provides two proximal corners. Specifically, edge 20 and edge 17 intersect to provide a first corner C1, edge 19 and edge 17 intersect to provide a second corner C2, edge 20 and edge 18 intersect to provide a third corner C3, and edge 19 and edge 18 intersect to provide a fourth corner C4.

In certain embodiments such as shown in FIG. 7, sample chamber 30 and thus entrance 32 is positioned very close to the distal edge of the sensor and about corners C1 and/or C2 and more specifically positioned close enough to the distal edge of the sensor so that a corner of the sensor may be contacted with a fluid drop of sample and the sample may be brought into the sample chamber. As shown, sample chamber 30 of FIG. 7 is slightly set back from sample application edge 17 of the sensor. As described above, this distance D of the subject test strips is minimized.

Figure 8:
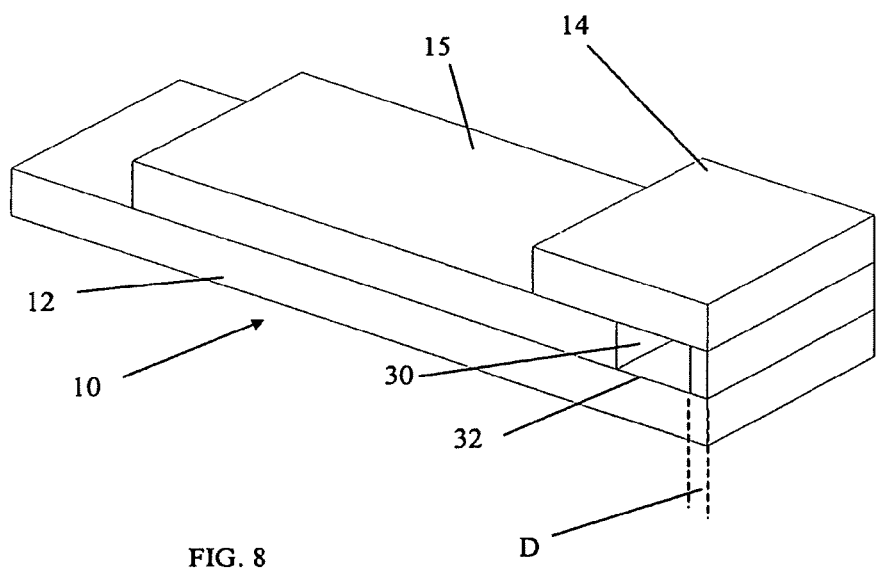
FIG. 8 shows a schematic exemplary embodiment of an analyte sensor according to the subject invention wherein the substrates and spacer layer are all of different lengths.

The dimensions of a sensor may vary. In certain embodiments, the overall length of a sensor of the invention may be no less than about 10 mm and no greater than about 50 mm. For example, the length may be between about 30 and 45 mm; e.g., about 30 to 40 mm. The lengths of the substrates that make a sensor may be the same or different. In certain embodiments, the width of sensor strip 10 may be no less than about 1 mm and no greater than about 15 mm. For example, the width may be between about 3 and 10 mm. In certain embodiments, a sensor may have a variable width (see for example the sensors of FIGS. 4, 5 and 6). In one particular example, sensor 10 has a length of about 30 mm and a width of about 6 mm. In a variable width embodiment, a sensor may have a length of about 30 mm and a width that ranges from about 2.5 mm to about 6 mm, e.g., a width of about 6 mm at the proximal end and a width of about 2.5 mm at the distal end. The thickness of substrates 12, 14 may be the same or different and may vary, where in certain embodiments the thickness of each substrate may be at least about 0.05 mm and generally no greater than about 3 mm, e.g., between about 0.20 mm and about 1 mm. In certain embodiments the thickness is about 0.25 mm. It is to be understood that both shorter and longer lengths for either or both substrate 12 and substrate 14 may be used, as may wider and/or thicker substrates 12, 14. As shown in FIG. 8, the substrates and/or spacer layer may all have different lengths (and/or widths).

Use of a corner-filled strip is particularly advantageous for alternate site testing (testing from a body site other than a finger tip, e.g., a forearm, leg, abdomen, etc.). For example, the corner-fill sensor may be rested near the alternate test site (for example a forearm) with a user contacting a corner of the sensor to the user's skin. As noted above, the sensor advantageously uses only a relatively small amount of body fluid sample for performing reliable tests, such as less than about 1 microliter, using a coulometric, amperometric, potientiometric, reflectrometic or other technique understood by those skilled in the art. This is significant for alternate site testing wherein typically a lower volume of sample is made available by a same lancing operation at an alternate site than when testing is performed on the finger.

Sensors 10 are generally configured for use with an electrical meter, which may be connectable to a PC or other electronics. The connection may be wired or wireless.

Sensors of the subject invention are particularly suited for inclusion in an 'integrated device', i.e., a device which has the sensor and at least a second element, such as a meter and/or a skin piercing element such as a lancet or the like, in the device. In some embodiments, a sensor may be integrated with both a meter and a lancet. Having multiple elements together in one device reduces the number of devices needed to obtain an analyte level and facilitates the sampling process.

For example, embodiments may include a housing that includes one or more of the subject sensors, a skin piercing element and a processor for determining the concentration of an analyte in a sample applied to the strip. A plurality of sensors may be retained in a cassette in the housing interior and, upon actuation by a user, a single sensor may be dispensed from the cassette so that at least a portion extends out of the housing for use.

The various components of the subject sensors are now described in greater detail.

Substrates

Sensor 10 has first and second substrates 12, 14, which are each non-conducting, inert substrates and which form the overall shape and size of the sensor. Substrates 12, 14 may be substantially rigid or substantially flexible. In certain embodiments, substrates 12, 14 are flexible or deformable. Examples of suitable materials for substrates 12, 14 include, but are not limited, to polyester, polyethylene, polycarbonate, polypropylene, nylon, and other "plastics" or polymers. In certain embodiments the substrate material is "Melinex" polyester. Other non-conducting materials may also be used such as paper, etc.

Spacer Layer

As indicated above, positioned between substrate 12 and substrate 14 is spacer 15. Spacer 15 separates first substrate 12 from second substrate 14. Spacer 15 is an inert non-conducting layer, typically at least as flexible and deformable (or as rigid) as substrates 12, 14. In certain embodiments, spacer 15 is an adhesive layer or double-sided adhesive tape or film. Any adhesive selected for spacer 15 should be selected to prevent or minimize diffusion or the release of material which may interfere with accurate analyte measurement.

The thickness of spacer 15 defines the depth of the sample chamber and may be dimensioned to provide a sample chamber having a capillary volume. In certain embodiments, the thickness of spacer 15 may be at least about 0.01 mm (10 µM) and no greater than about 1 mm or about 0.5 mm. For example, the thickness may be between about 0.02 mm (20 µm) and about 0.2 mm (200 µm). In certain embodiments, the thickness is about 0.05 mm (50 µm), and about 0.1 mm (100 µm) in another embodiment.

The length of spacer 15 may be less or greater than the length of substrate 12 and/or of substrate 14 (see for example FIG. 8 in which at least the length of spacer 15 is less than at least one of the substrates), and/or the spacer and one or both substrates may be displaced along their longitudinal axes. The width of spacer 15 may be the same or different than the widths of the substrates, where in many embodiments the width is generally the same as the width of substrate 12 and substrate 14.

Sample Chamber

As described above, the sensors according to the subject invention include a sample chamber 30 for receiving a volume of sample to be analyzed, which chamber includes one or more sample chamber entrances positioned about one or more intersecting edges of the sensor. Sample chamber 30 is configured so that when a sample is provided in chamber 30, the sample is in electrolytic contact with both the working electrode and the counter electrode, which allows electrical current to flow between the electrodes to effect the electrolysis (electrooxidation or electroreduction) of the analyte. As noted above and as shown, for example, in FIG. 7, sample chamber 30 is defined, in part, by substrate 12, substrate 14 and by spacer 15.

Sample chamber 30 has a volume sufficient to receive a sample of biological fluid therein. In some embodiments, such as when sensor 10 is a small volume sensor, sample chamber 30 has a volume that is no more than about 1 µL, for example no more than about 0.5 µL, and also for example, no more than about 0.25 µL. A volume of no more than about 0.1 µL is also suitable for sample chamber 30, as are volumes of no more than about 0.05 µL and no more than about 0.03 µL. Sample chamber 30 has dimensions that facilitate drawing sample to be analyzed into sample chamber 30 by capillary or other surface tensions forces. In embodiments that include spacer 15 between substrates 12, 14, the thickness of sample chamber 30 is generally the thickness of spacer 15.

A measurement zone (not shown) is contained within sample chamber 30 and is the region of the sample chamber that contains only that portion of the sample that is interrogated during the analyte assay. In some embodiments, the measurement zone has a volume that is approximately equal to the volume of sample chamber 30. In some embodiments the measurement zone includes 100% of the sample chamber or less, e.g., about 90% or less, e.g., about 80% or less, e.g., about 75% or less. In certain embodiments, an accurate measurement of the sample may be obtained with only a partial filling of the sample chamber, but complete filling of the measurement zone, as described in the aforementioned patent application Ser. No. 11/225,659.

Electrodes

Figure 9:
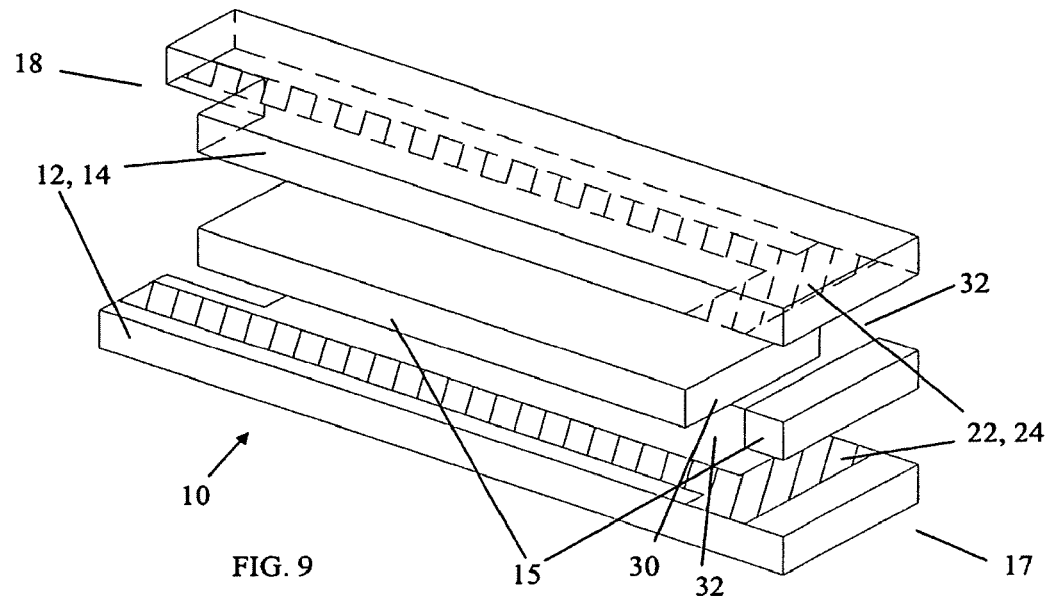
FIG. 9 shows an exploded view of a schematic exemplary embodiment of an analyte sensor according to the subject invention having oppositely oriented, spaced-apart electrodes.
Figure 10:
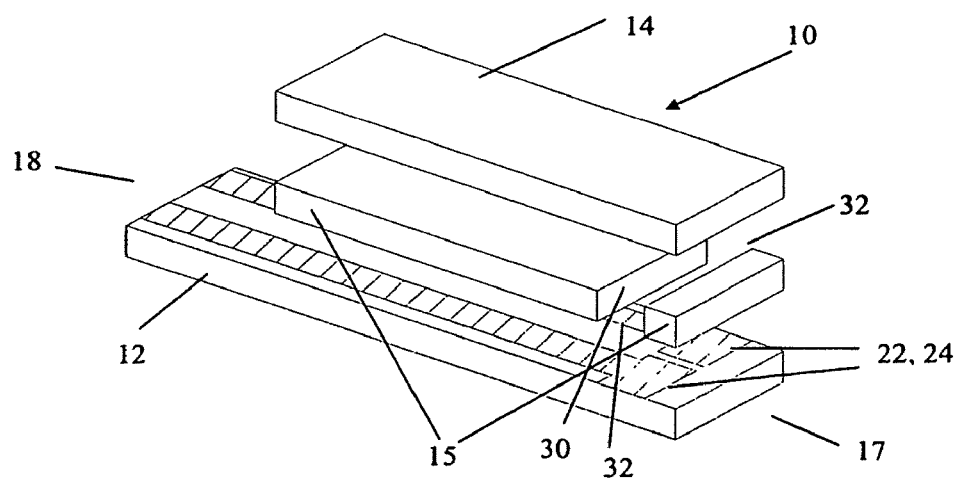
FIG. 10 shows an exploded view of a schematic exemplary embodiment of an analyte sensor according to the subject invention having coplanar electrodes.

The sensor includes a working electrode and at least one counter electrode. The counter electrode may be a counter/reference electrode. If multiple counter electrodes are present, one of the counter electrodes will be a counter electrode and one or more may be reference electrodes. FIGS. 9 and 10 show two exemplary electrode configurations.

Working Electrode

At least one working electrode is positioned on one of first substrate 12 and second substrate 14 of sensor 10. In these particular embodiments, working electrode 22 is illustrated on substrate 12 for exemplary purposes only. Working electrode 22 has a portion present in the area of sample chamber 30, and in some embodiments, includes a conductive trace that extends from the sample chamber to an end 18 of the sensor, such as for connecting to a meter.

Working electrode 22 may be a layer of conductive material such as any suitable conductive material, e.g., gold, carbon, platinum, ruthenium dioxide, palladium, or other non-corroding, conducting material. Working electrode 22 may be a combination of two or more conductive materials. An example of a suitable conductive epoxy is ECCOCOAT CT5079-3 Carbon-Filled Conductive Epoxy Coating (available from W. R. Grace Company, Woburn, Mass.). The material of working electrode 22 typically has relatively low electrical resistance and is typically electrochemically inert over the potential range of the sensor during operation.

Working electrode 22 may be applied on substrate 12 by any of various methods. Electrode 22 may be deposited, such as by vapor deposition or vacuum deposition or otherwise sputtered, printed on a flat surface or in an embossed or otherwise recessed surface, transferred from a separate carrier or liner, etched, or molded. Suitable methods of printing include but are not limited to screen-printing, piezoelectric printing, ink jet printing, laser printing, photolithography, and painting.

As described above, at least a portion of working electrode 22 is provided in sample chamber 30 for the analysis of analyte, in conjunction with the counter electrode 24.

Counter Electrode

The sensor includes at least one counter electrode positioned within the sample chamber. In FIG. 8, counter electrode 24 is illustrated on substrate 14 to provide a sensor having oppositely-oriented, spaced-apart electrodes and in FIG. 9, a counter electrode 24 is present on substrate 12 to provide a sensor having co-planar electrodes. Counter electrode 24 has a portion present in the area of sample chamber 30, and in some embodiments, includes a conductive trace that extends from the sample chamber portion to an end 18 of the sensor, such as for connecting to a meter.

Counter electrode 24 may be constructed in a manner similar to working electrode 22. The same materials and methods may be used to make counter electrode 24 as are available for constructing working electrode 22, although different materials and methods may also be used. Counter electrode 24 may include a mix of multiple conducting materials, such as Ag/AgCl and carbon.

Electrode Configurations

Working electrode 22 and counter electrode 24 may be disposed opposite to and facing each other to form facing electrodes. See for example, FIG. 9, which has working electrode 22 on substrate 12 and counter electrode 24 on substrate 14, forming facing electrodes. Working electrode 22 and counter electrode 24 may alternately be disposed generally planar to one another, such as on the same substrate, to form co-planar or planar electrodes. Referring to FIG. 10, both working electrode 22 and counter electrode 24 occupy a portion of the surface of substrate 12, thus forming co-planar electrodes.

Indicator Electrode

A sensor may include at least one indicator electrode (not shown) positioned on the first substrate 12 and/or the second substrate 14. An indicator electrode is used to detect when sample chamber 30 has been sufficiently filled with sample, to prevent partial filling of measurement zone 30.

An indicator electrode may be constructed in a manner similar to working electrode 22 and/or counter electrode 24. Suitable materials and methods for an indicator electrode include the same materials and methods as used for working electrode 22 and/or counter electrode 24, although different materials and methods may also be used. For example, carbon is a material that may be used for an indicator electrode.

In certain embodiments, an indicator electrode may be positioned in sample chamber 30 with at least working electrode 22 positioned between it and an entrance to the sample chamber. In most embodiments, counter electrode 24 will also be positioned between the indicator electrode and the chamber entrance. An indicator electrode is so positioned so that that biological fluid sample, upon entering sample chamber 30 via chamber entrance 32, flows past working electrode 22 prior to contacting the indicator electrode.

Upon the sample contacting the indicator electrode, the indicator electrode is the source of a signal to an attached meter. Suitable signals include, for example, voltage, current, resistance, impedance, or capacitance. The signal indicates to the meter, and/or the user, that there is sufficient sample in the measurement zone to begin the assay. This indication may be a visual sign and/or auditory signal and/or vibratory signal, or the meter may be configured to automatically initiate the assay.

Chemistry

Redox Mediator

Chemistry (also referred to as sensing chemistry, analyte-responsive chemistry or reagent) is provided for the analysis of the analyte. This sensing chemistry may include a redox mediator and a second electron transfer mediator, although in some instances, one or the other may be used alone. The redox mediator and second electron transfer agent may be independently diffusible or leachable, or non-diffusible or non-leachable, such that either or both may be diffusible or leachable or not. For purposes of discussion herein, the term "diffusible" will be used to represent "diffusible or leachable" and the term "non-diffusible" will be used to represent "non-diffusible or non-leachable" and variations thereof. The redox mediator may be air oxidizable.

Placement of chemistry components may depend on a variety of factors, e.g., whether they are diffusible or not. For example, both non-diffusible and/or diffusible component(s) may form a sensing layer on working electrode 22. Alternatively, one or more diffusible components may be present on any surface in sample chamber 30 prior to the introduction of the sample to be analyzed. As another example, one or more diffusible component(s) may be placed in the sample prior to introduction of the sample into sample chamber 30.

If the redox mediator is non-diffusible, then the redox mediator may be disposed on working electrode 22 as, for example, a layer. In an embodiment having a redox mediator and a second electron transfer agent, if the redox mediator and second electron transfer agent are both non-leachable, then both components may be disposed on working electrode 22 as individual layers, or combined and applied as a single layer.

The redox mediator, whether it is diffusible or not, mediates a current between working electrode 22 and the analyte and enables the electrochemical analysis of molecules which may not be suited for direct electrochemical reaction on an electrode. The mediator functions as an electron transfer agent between the electrode and the analyte.

Any suitable chemistry may be employed in the sensors of the subject invention. For example, a redox mediator that may be employed is a transition metal compound or complex. Examples of suitable transition metal compounds or complexes include but are not limited to osmium, ruthenium, iron, and cobalt compounds or complexes. In these complexes, the transition metal is coordinatively bound to one or more ligands, which are typically mono-, di-, tri-, or tetradentate. The redox mediator can be a polymeric redox mediator, or, a redox polymer (i.e., a polymer having one or more redox species). Examples of suitable redox mediators and redox polymer are disclosed, e.g., in U.S. Pat. Nos. 6,338,790, 6,605,200 and 6,605,201.

Second Electron Transfer Agent

As noted above, a sensor of the subject invention may include a redox mediator and a second electron transfer agent that is capable of transferring electrons to or from the redox mediator and the analyte. The second electron transfer agent may be diffusible or non-diffusible. One example of a suitable second electron transfer agent is an enzyme which catalyzes a reaction of the analyte. For example, a glucose oxidase or glucose dehydrogenase, such as pyrroloquinoline quinone glucose dehydrogenase (PQQ), is used when the analyte is glucose. Other enzymes may be used for other analytes. These enzymes catalyze the electrolysis of an analyte by transferring electrons between the analyte and the electrode via the redox mediator.

Manufacture of the Sensors

Sensor embodiments described above, are sandwiched or layered constructions having substrates 12, 14 spaced apart, such as by spacer 15. Such a construction may be made by laminating the various layers together in any suitable manner, or made using any suitable method. Sensors of the subject invention may be molded.

Molding may include positioning at least two spaced apart, electrically conductive electrodes (e.g., wires) in a mold, and molding a body of insulative material around the electrodes, so that at least one sample chamber opening is provided about a corner of the sensor. More specifically, molding may include positioning at least two spaced apart, electrically conductive electrodes (e.g., wires) in a mold, before or after molding, treating at least one of the electrodes with one or more chemicals to change the electrical properties of the treated electrode upon contact with a fluid sample, and molding a body of insulative material around the electrodes with one end having at least one sample chamber opening is provided about a corner of the sensor. The body may be molded in multiple pieces, e.g., two pieces, with a body and end cap for attaching to one another after the molding is completed, or in a single piece.

Methods

Also provided are methods of analyte determination. In general, by contacting a corner of the sensor with a sample of biological fluid, the sample is admitted into the sample chamber of the sensor, where the level of analyte is determined. Analytes include, but are not limited to those described herein. In certain embodiments, it is the level of glucose in blood or interstitial fluid that is determined. In many embodiments, the source of the biological fluid is a drop of blood drawn from a patient, e.g., after piercing the patient's skin with a lancing device or the like, which may be present in an integrated device in certain embodiments, together with a sensor of the subject invention.

Accordingly, embodiments include piercing an area of skin to cause blood to flow from the pierced site and contacting the blood at the site with a corner of a sensor, thereby enabling blood to enter the sample chamber for analysis. In certain embodiments, capillary forces may pull the sample into the chamber.

Typically, the sensor, either before sample contact or after, is connected to a meter, e.g., a meter as described in U.S. Pat. Nos. 6,924,518 and 6,893,545. In certain embodiments, the corner-fill sensor is operatively connected to a meter prior to contacting a corner of the sensor to a sample to be tested, thereby making the sensor and meter easier and more convenient to use. Also for ease of use and convenience, in many embodiments, an opening in skin at the testing site (e.g., a finger or alternative testing site (e.g., forearm, abdomen, or the like)) to obtain analyte-containing-body fluid to be tested, may be created after the sensor is connected to the meter.

The meter to which the sensor is attachable may be programmed to monitor for when a signal from an indicator electrode (if present) is received, thus indicating if and when sample has contacted the indicator electrode. When the signal is received, a sufficient amount of sample has entered the sample chamber to ensure that the measurement zone is adequately filled, e.g., in embodiments in which an indicator electrode is downstream (closest to the meter end of the sensor than the sample filling end of the sensor) of the working electrode and the measurement zone. The signal may be an on/off signal, or may be a change (either an increase or decrease) in an existing signal.

Upon termination of contact of the sensor corner with the sample source, e.g., a drop of blood, the sample within sample chamber may stop flowing and may remain stationary. The dimensions of sample chamber may inhibit the sample from moving without the source and the sample may thus remain in the chamber in a generally non-flowing state. During the analysis, which may take as little as about 5 seconds or less, e.g., 3 seconds or less, or as much as about 30 seconds or more, it may be desirable, depending on the configuration of the sensor, that the sample may be non flowing in the sample chamber.

Embodiments of the subject methods include determining the concentration of an analyte in any volume of sample, and include determining analyte concentration in a small volume of sample, e.g., a sample having a volume no more than about 1 µL, for example no more than about 0.5 µL, for example no more than about 0.25 µL, for example no more than about 0.1 µL. In some embodiments, methods include determining the concentration of an analyte a volume of sample as low as about 0.05 µL or as low as about 0.03 µL. The sensors of the subject invention may be configured as those described in U.S. patent application Ser. No. 11/225,659, in which an accurate analyte measurement may be obtained using a volume of sample that wholly or partially fills the sample chamber.

Embodiments of the subject methods include admitting a volume of biological fluid to a sample chamber having a particular volume capacity sufficient to receive a sample of biological fluid therein. In some embodiments, methods include admitting a volume of sample to a the sample chamber that has a volume that is no more than about 1 µL, for example no more than about 0.5 µL, for example no more than about 0.25 µL, for example no more than about 0.1 µL, for example no more than about 0.05 µL, for example no more than about 0.03 µL. Sample chamber may have dimensions that facilitate drawing sample to be analyzed into sample chamber by capillary or other surface tensions forces.

Analyte determination may be accomplished using any suitable technique. For example, the analyte assay may be accomplished using coulometry, amperometry and/or potentiometry or reflectometry. In certain embodiments, the measurement technique includes impedance measurement. Certain embodiments may include using photometric techniques. The method of calculation will be a function of the meter and other electronics configured for use with the sensor. Details regarding meters, electronics, and calculation methods are described, for example, in U.S. Pat. No. 6,338,790 and elsewhere.

A sensor may be operated with or without applying a potential to electrodes 22, 24. In one embodiment, in which the sensor is an electrochemical sensor (the subject invention also includes optical sensors), the electrochemical reaction may occur spontaneously and a potential need not be applied between the working electrode and counter electrode of the sensor. In another embodiment, a potential may be applied between the working electrode and counter electrode of the sensor. The potential may be constant or not, and the magnitude of the potential is dependent at least in part on the redox mediator. As above, details regarding potential as related to the sensing chemistry and the electrodes are discussed, for example, in U.S. Pat. No. 6,338,790 and elsewhere.

In certain embodiments, the results of an analyte reading (processed or not) may be forwarded (such as by communication) to a remote location if desired, and received there for further use (such as further processing). By "remote location" is meant a location other than the location at which the sample evaluation device is present and sample evaluation occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, Internet, etc.

Kits

Finally, kits for use in practicing the subject invention are also provided. The subject kits may include one or more corner-fill sensors as described herein. Embodiments may also include a skin-piercing element, e.g., a lancing device or the like.

The kits may further include one or more additional components necessary for carrying out an analyte determination assay, such as control reagents, and the like. As such, the kits may include one or more containers such as vials or bottles, with each container containing a separate component for the assay.

In addition to one or more corner-fill sensors, the subject kits may also include written instructions for using a corner-fill sensor to contact fluid with a corner of the sensor for use in an analyte determination assay such as a glucose assay. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g. via the Internet, are provided. An example of this embodiment is a kit that includes a web address where the instructions can be viewed and/or from which the instructions can be downloaded. As with the instructions, this means for obtaining the instructions is recorded on a suitable substrate.

In many embodiments of the subject kits, the components of the kit are packaged in a kit containment element to make a single, easily handled unit, where the kit containment element, e.g., box or analogous structure, may or may not be an airtight container, e.g., to further preserve the one or more sensors and additional reagents (e.g., control solutions), if present, until use.

It is evident from the above results and discussion that the above-described invention provides devices and methods for admitting sample to a sample chamber of a sensor by contacting the sample with a corner of the sensor. The above-described invention provides a number of advantages—some of which are described above and which include, but are not limited to, ease of use and ease of manufacture. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present inven-

What is claimed is:

1. A sensor for determining the concentration of a ketone body in a sample of biological fluid, the sensor comprising:
   a working electrode and a counter electrode;
   a first corner of the sensor at the intersection of a first side edge and a distal edge of the sensor and a second corner of the sensor at the intersection of a second side edge and the distal edge of the sensor; and
   a sample chamber for receiving biological fluid, wherein the sample chamber only has a first and a second entrance for admitting the biological fluid, the first entrance positioned at the first corner and the second entrance positioned at the second corner,
   wherein the sample chamber is adapted to receive the biological fluid by contacting the first corner or the second corner of the sensor with the biological fluid.

2. The sensor of claim 1, wherein the sensor is adapted to determine the concentration of an analyte using about 1 μL or less of sample in the sample chamber.

3. The sensor of claim 1, wherein the sample chamber is configured to contain no more than about 1 μL of sample.

4. The sensor of claim 1, wherein the corners are substantially rounded.

5. The sensor of claim 1, wherein the corners are substantially squared.

6. A sensor for determining the concentration of a ketone body in a biological fluid sample, the sensor comprising:
   a first side edge, a second side edge, a proximal edge and a distal edge, wherein the distal edge is parallel to the proximal edge;
   a first corner of the sensor at the intersection of the first side edge and the distal edge of the sensor and a second corner of the sensor at the intersection of the second side edge and the distal edge of the sensor; and
   a sample chamber adapted to determine the concentration of a ketone body in less than about 1 μL of sample, wherein the sample chamber only has a first and a second chamber opening for admitting the sample to the sample chamber;
   wherein the first chamber opening is positioned at the first corner and the second chamber opening is positioned at the second corner of the sensor.

7. The sensor of claim 6, wherein the sensor is formed in a substantially rectangular shape.

8. The sensor of claim 6, wherein the sensor is adapted to determine the concentration of a ketone body using about 0.5 μL or less of sample in the sample chamber.

9. The sensor of claim 8, wherein the sensor is adapted to determine the concentration of a ketone body using about 0.2 μL or less of sample in the sample chamber.

10. The sensor of claim 8, wherein the sensor is adapted to determine the concentration of a ketone body using about 0.1 μL or less of sample in the sample chamber.

11. The sensor of claim 6, wherein the sample chamber is configured to contain no more than about 1 μL of sample.

12. The sensor of claim 11, wherein the sample chamber is configured to contain no more than about 0.5 μL of sample.

13. The sensor of claim 12, wherein the sample chamber is configured to contain no more than about 0.2 μL of sample.

14. The sensor of claim 13, wherein the sample chamber is configured to contain no more than about 0.1 μL of sample.

15. The sensor of claim 6, wherein the sensor is an electrochemical sensor.

16. The sensor of claim 6, wherein the sensor is an optical sensor.

17. The sensor of claim 6, wherein the proximal edge is operatively connectable with a meter.

18. The sensor of claim 6, wherein the distance between a sample chamber edge and the distal edge ranges from about 0.01 mm to about 1.5 mm.

19. A ketone body sensor comprising:
   a first substrate separated from a second substrate by a spacer layer and including at least one electrode, the first and second substrates forming a sensor comprising a first side edge opposite to a second side edge, a distal edge opposite and parallel to a proximal edge, wherein the distal edge is shorter than the proximal edge;
   a first corner of the sensor at the intersection of the first side edge and the distal edge of the sensor and a second corner of the sensor at the intersection of the second side edge and the distal edge of the sensor;
   a sample chamber; and
   only a first and a second chamber opening for admitting sample to the sample chamber, wherein the first sample chamber opening is located at the first corner and the second sample chamber opening is located at the second corner of the sensor.

20. A method for determining a ketone body concentration in a sample of biological fluid, the method comprising:
   a working electrode and a counter electrode;
   a first corner of the sensor at the intersection of a first side edge and a distal edge of the sensor and a second corner of the sensor at the intersection of a second side edge and the distal edge of the sensor; and
   a sample chamber for receiving biological fluid, wherein the sample chamber includes at least a portion of the working and counter electrodes and wherein the sample chamber only has a first and a second entrance for admitting the biological fluid, the first entrance positioned at the first corner and the second entrance positioned at the second corner,
   wherein the sample chamber is adapted to receive the biological fluid by contacting the first corner or the second corner of the sensor with the biological fluid;
   applying, after connecting the sensor to the meter, an ketone body-containing sample to the analyte sensor by contacting the first or the second corner of the sensor with the sample; and
   determining the concentration of a ketone body in the sample.

21. The method of claim 20, wherein the concentration of the ketone body is determined using about 1 μL or less of sample in the sample chamber.

22. The method of claim 21, wherein the concentration of the ketone body is determined using about 0.5 μL or less of sample in the sample chamber.

23. The method of claim 22, wherein the concentration of the ketone body is determined using about 0.2 μL or less of sample in the sample chamber.

24. The method of claim 23, wherein the concentration of the ketone body is determined using about 0.1 μL or less of sample in the sample chamber.

25. The method of claim 20, wherein the sample chamber is sized to contain no more than about 1 μL of sample.

26. The method of claim 20, wherein the ketone body concentration is determined using photometry.

27. The method of claim 20, wherein the determining comprises a measurement technique involving an electrochemical measurement in the sensor.

28. The method of claim 27, wherein the measurement technique comprises amperometry.

29. The method of claim 27, wherein the measurement technique comprises coulometry.

30. The method of claim 27, wherein the measurement technique comprises potentiometry.

31. The method of claim 27, wherein the measurement technique comprises impedance measurement.

32. An integrated device for determining the concentration of a ketone body in sample, the system comprising:
   a housing comprising a sensor and a processor adapted for determining the concentration of a ketone in a sample applied to the sensor, the sensor comprising:
   a working electrode and a counter electrode;
   a first corner of the sensor at the intersection of a first side edge and a distal edge of the sensor and a second corner of the sensor at the intersection of a second side edge and the distal edge of the sensor; and
   a sample chamber, wherein the sample chamber includes at least a portion of the working and counter electrodes and wherein the sample chamber only has a first and a second entrance for admitting sample to the sample chamber, the first entrance positioned at the first corner and the second entrance positioned at the second corner,
   wherein the sample chamber is adapted to receive the sample by contacting the first corner or the second corner of the sensor with the biological fluid.

33. The sensor of claim 1, wherein the sample chamber is configured to contain no more than about 0.5 µL of sample.

34. The sensor of claim 1, wherein the first side edge and the second side edge are parallel to each other.

* * * * *